(12) United States Patent
Stevens

(10) Patent No.: US 6,960,181 B2
(45) Date of Patent: Nov. 1, 2005

(54) IRRIGATION DRESSING WITH A TUBULAR DAM

(75) Inventor: Robert C. Stevens, Gainesville, FL (US)

(73) Assignee: Carol J. Stevens, Gainesville, FL (US)

( * ) Notice: Subject to any disclaimer, the term of this patent is extended or adjusted under 35 U.S.C. 154(b) by 0 days.

(21) Appl. No.: 10/277,319

(22) Filed: Oct. 22, 2002

(65) Prior Publication Data

US 2004/0078011 A1 Apr. 22, 2004

(51) Int. Cl.$^7$ .................................................. A61F 13/00
(52) U.S. Cl. ..................................... 604/30 S; 604/308
(58) Field of Search ............................... 604/304–308; 128/888, 856

(56) References Cited

U.S. PATENT DOCUMENTS

| | | | |
|---|---|---|---|
| 3,026,874 A | | 3/1962 | Stevens |
| 5,395,675 A | * | 3/1995 | Altholz et al. ................. 428/45 |
| 5,741,235 A | * | 4/1998 | Knight ......................... 604/174 |
| 5,779,657 A | | 7/1998 | Daneshvar |
| 5,951,502 A | | 9/1999 | Peeler et al. |
| 5,960,497 A | | 10/1999 | Castellino et al. |
| 5,991,654 A | | 11/1999 | Tumey et al. |
| 6,135,116 A | | 10/2000 | Vogel et al. |
| 6,142,982 A | | 11/2000 | Hunt et al. |
| 6,398,767 B1 | * | 6/2002 | Fleischmann ................ 604/313 |
| 6,447,460 B1 | | 9/2002 | Zheng et al. |

OTHER PUBLICATIONS

When Wounds Won't Heal, by Susan Mendez–Eastman, RN; RN Magazine, pp. 2–5, Jan. 1998.
A Simplified Method of Care for Gastrointestinal Fistual, by Gary, et al., SURGERY Magazine, pp. 1–3, Jan. 1962.

* cited by examiner

*Primary Examiner*—Larry L Schwartz
*Assistant Examiner*—Linh Truong
(74) *Attorney, Agent, or Firm*—Fay, Sharpe, Fagan, Minnich & McKee, LLP (57) ABSTRACT

An irrigation dressing is provided including a hollow inflatable tubulardam with a central opening adapted to surround the wound of the individual. A semi-hard resilient clear plastic window is attached to the dam, such that the central opening is completely enclosed on a front surface of the dam. The dressing includes an inner peripheral ridge and an outer peripheral ridge extending beyond a bottom or back body-engaging surface of the dam which facilitates drawing a vacuum. A plurality of connectors are attached to a front planar face surface of the clear plastic window. At least one connector is pivotable about an axis parallel to the front planar surface of the window. A self-sealing plug is disposed inside the dam so that the dam can be inflated to selected pressures using an associated hypodermic needle or the like.

32 Claims, 6 Drawing Sheets

IRRIGATION DRESSING WITH A TUBULAR DAM

FIELD OF THE INVENTION

The present invention relates generally to medical treatment of wounds, and more particularly to an improved wound shield and irrigation dressing for treating wounds to promote the overall healing process and to discourage enteric fistula and wound infections.

BACKGROUND OF THE INVENTION

Wound shields for treating enteric fistula and wound infections are known. The express purpose of these prior devices is to provide an irrigation dressing for patients as a replacement for the typical gauze type dressings. It is well known that gauze type dressings are not only messy, but result in constant re-opening of the wounds when the dressings are changed, which could cause infections and delay the healing process. Further, dressing changes usually cannot be performed by the patient alone. They are often quite painful to the patient, expensive, and not conducive to providing frequent irrigation of the wound with medical solutions.

One known prior art irrigation dressing proposed to alleviate the problems associated with gauze type dressings is shown in expired U.S. Pat. No. 3,026,874. The device taught in that patent provides a wound shield that forms a dam around a wound and includes a clear flexible plastic window or cover for observing the healing process. The dam is fabricated of a continuous loop of foam rubber. To facilitate flushing and air control, several holes are provided at selected locations along the perimeter of the shield. The device is held in place using belts and snap fasteners that are rigidly attached to the wound shield.

Although the wound shield described above is preferred over gauze dressings, the foam rubber dam is too rigid for good sealing qualities. Further, the overall wall depth of the device is too shallow to accommodate adequate irrigation solution volumes. Lastly, the dam often comes into contact with the wound thus disrupting the healing process.

Figure 1:
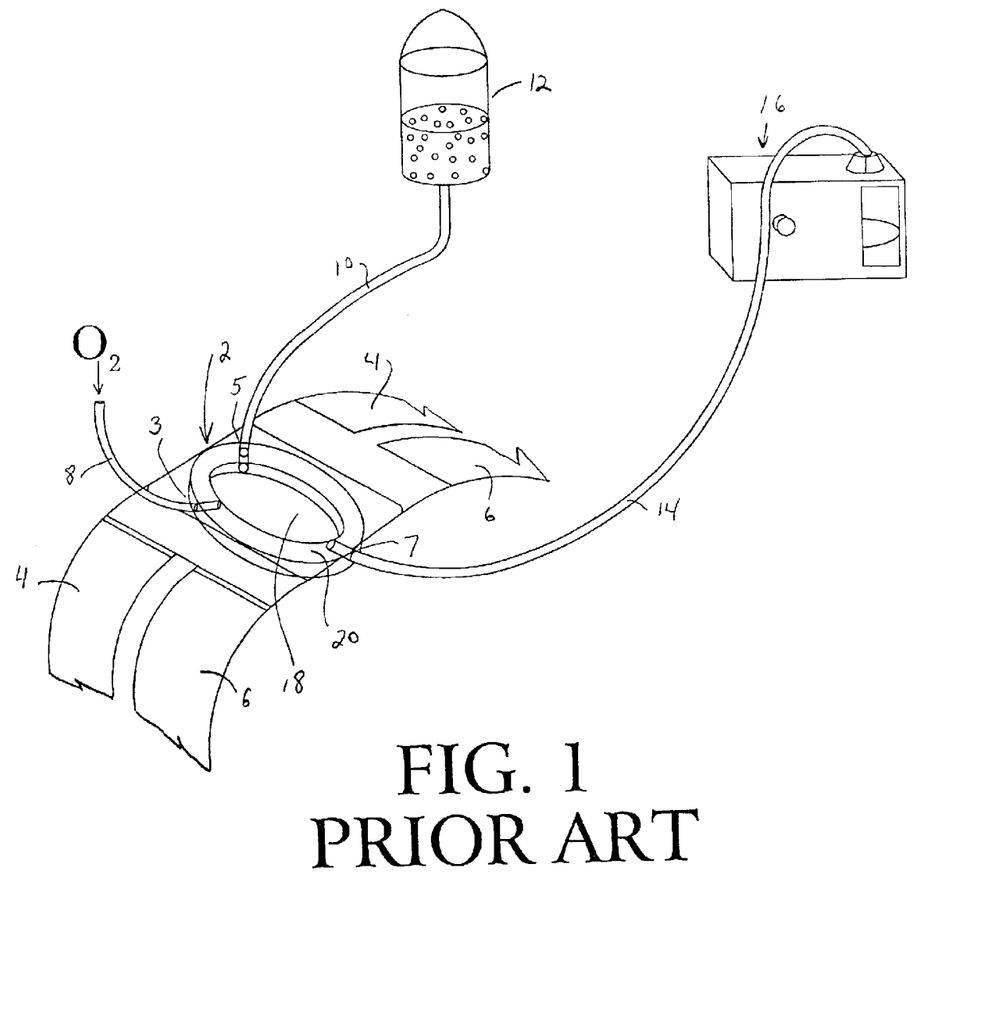
FIG. 1 is a perspective view of a prior art wound dressing device.

A modified wound shield or irrigating dressing is shown in FIG. 1. Wound shield 2 includes a generally oval shaped dam 20 and a window 18 attached over the top of the dam 20. The shield is secured to a patient by a first belt 4 and a second belt 6. The ends of the belts 4 and 6 are rigidly connected to window 18 by snap fasteners. Dam 20 includes an irrigation aperture 3 adapted to receive a tube 10 connected on a remote end to a supply of irrigation solution 12. Dam 20 includes a drying aperture 3 adapted to receive a tube 8 connected on a remote end to a supply of oxygen, and a draining aperture 7 adapted to receive a tube 14 connected to an associated pump 16.

In use of the above device, a flow of irrigation solution constantly irrigates the wound on the patient by a timer control, patient control, or care giver control. Oxygen or air is alternately supplied into the shield to dry the wound, while pump 16 removes the irrigation solution from the enclosed area. The wound is visible through window 18 as it heals without being exposed to contaminants. The dressing can be used for about two weeks before changing is required.

The dam of the wound shield described above comprises a hollow, highly flexible tube, which is inflated with air prior to or during use. The desired firmness is obtained by controlling the pressure of air within the dam.

Although the wound dressing is modestly successful in treating patients, the device requires a fair amount of readjustment after it is installed on the patient because the dressing twists and bends with movement of the patient. This is primarily due to a lack of flexibility in the wound shield. Further, the device tends to buckle in the middle due to a lack of cross-sectional rigidity in the inflatable dam section. This causes leakage from under the wound shield as well as undesirable contact between the wound and the window.

Therefore, it would be desirable to provide an irrigation dressing that is less rigid to prevent separation from the skin of the patient as the patient moves. The irrigation dressing should not be too soft so that it crumples with patient movement.

It is also desirable to provide an irrigation dressing that can be readily used with vacuum assist closure (VAC) devices for applying a vacuum to a wound.

It is further desirable to provide an irrigation dressing system that can conform to the shape of a moving patient yet retaining its fluid containment and vacuum integrity.

SUMMARY OF THE INVENTION

In accordance with a preferred embodiment of the invention, a wound shield and irrigation dressing system is provided to be worn on ambulatory patients for protecting and enclosing wounds. The wound shield allows for frequent irrigation of the wound with an irrigation solution and alternate frequent drying of the wound, while also providing for drainage of the irrigation solution and selective application of a vacuum to the wound.

The wound shield includes a hollow inflatable tubular dam formed of an inner peripheral surface defining a central opening adapted to surround the wound of the individual, an outer peripheral surface defining the outermost extremity of the dam, a bottom body-engaging surface and a top surface connecting said inner and outer peripheral surfaces to one another. A somewhat stiff clear plastic window is provided having generally flat front and rear planar surfaces. The flat rear planar surface of the window is attached to the top surface of the dam, so that a central cavity opening is defined under the window and surrounded by the oval dam.

In a preferred aspect of the invention, the wound shield includes an inner peripheral ridge extending from the inner peripheral surface beyond the bottom body-engaging surface of the dam downwardly away from the window. An outer peripheral ridge is formed on the tubular dam extending from the outer peripheral surface beyond the bottom body-engaging surface of the dam downwardly away from the window. The ridges on the bottom or rear side of the device provide an overall elongate "U-shaped" contact surface for contacting the skin, eliminating the need to apply skin adhesives to the patient, while also sealing in fluids and eliminating vacuum loss. The ridges also play an important part in improving the cross-sectional rigidity of the dam and for preventing fluid leakage. Ridges can also extend from the front or top surface of the dam aiding in the adhesion of the dam to the window, and adding to the overall cross-sectional rigidity of the dam.

In another preferred aspect of the invention, the wound shield includes a plurality of connectors attached to the front planar surface of the clear plastic window. Each connector is disposed at different locations outside the central opening of the dam, and each is adapted to be releasably attached to a connecting end of a belt. The connectors are pivotable about an axis parallel to the front planar surface of the window.

In yet another preferred aspect of the invention, the subject wound shield includes a resilient self-sealing plug disposed inside the dam. The plug is adapted to receive a hypodermic needle, whereby air can be forced into the dam through the hypodermic needle causing the dam to inflate. The plug is "self healing" and seals itself upon removal of the hypodermic needle, so that the fluid containment integrity of the dam is not compromised. Precise control over the pressure within the dam is thereby enabled.

An object of the present invention is to provide an improved wound shield with pivoting belt connectors that allow for patient movement without the need for readjustment of the wound shield.

A further object is to provide a wound shield with one or more radial ribs disposed on the perimeter of the dam to prevent fluid leakage from out of the central cavity. It is yet another object of the invention to provide a wound shield with an improved cross-sectional rigidity.

A further object is to provide an airtight dam facilitating vacuum assisted closure (VAC). The irrigating dressing is particularly useful with this technique because the wound can be thoroughly cleaned with fluids and thoroughly dried with air using the device before vacuum is applied. The wound can be treated with VAC without irrigation.

It is another object of the invention to provide a wound shield having an inflatable dam with an improved inflating device for precise control over the fluid pressure within the dam.

Another object of the invention is to provide a wound shield that enables frequent wound cleansing, drying and drainage, while also being easy to use and maintained by care givers and patients.

Another object is to make the patient ambulatory while wearing the device.

These and other objects will become apparent from the following description of the preferred embodiments taken together with the accompanying drawings and appended claims.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein.

DETAILED DESCRIPTION OF THE PREFERRED EMBODIMENT

Figure 2:
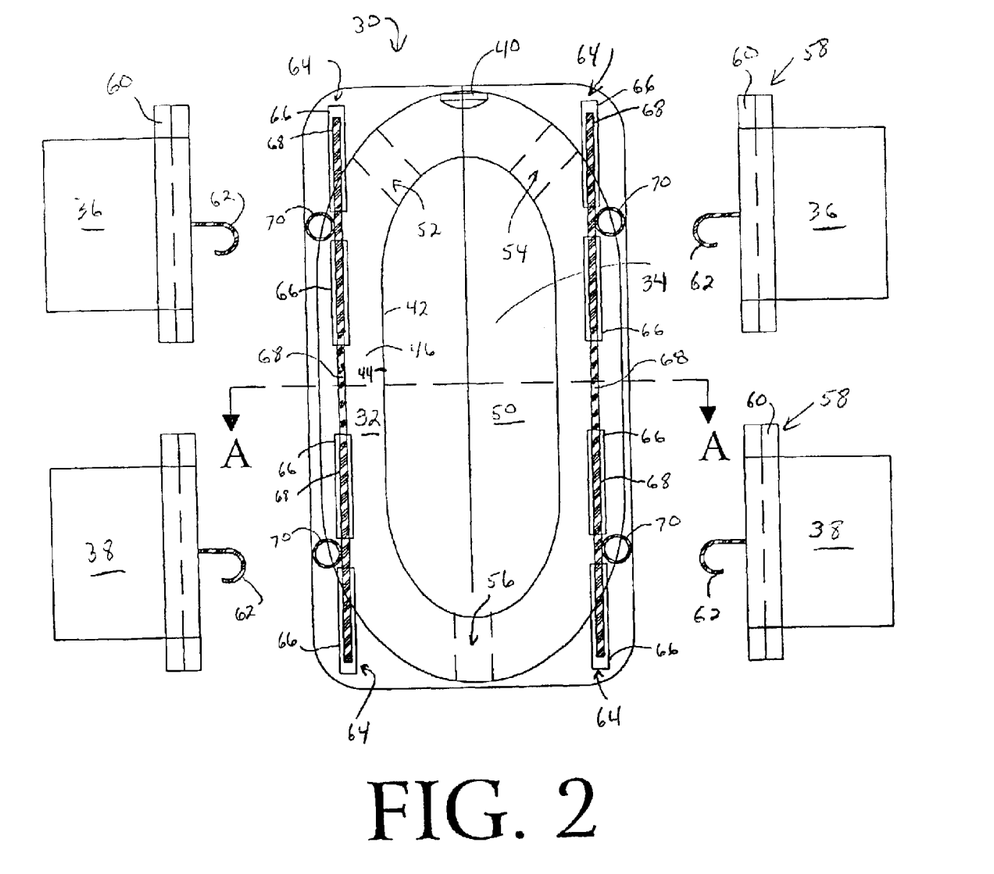
FIG. 2 is a top view of a preferred wound shield and a preferred belt arrangement in accordance with the present invention.
Figure 3:
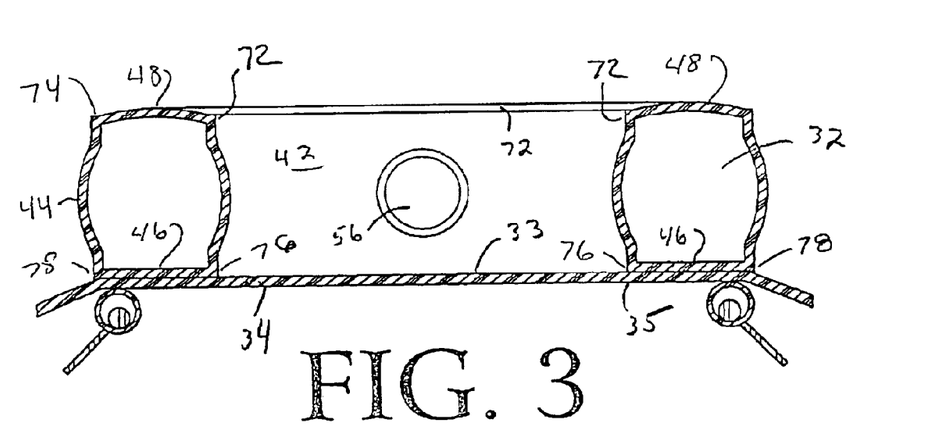
FIG. 3 is a cross-sectional view taken along the line A—A of the preferred wound shield shown in FIG. 2.
Figure 4:
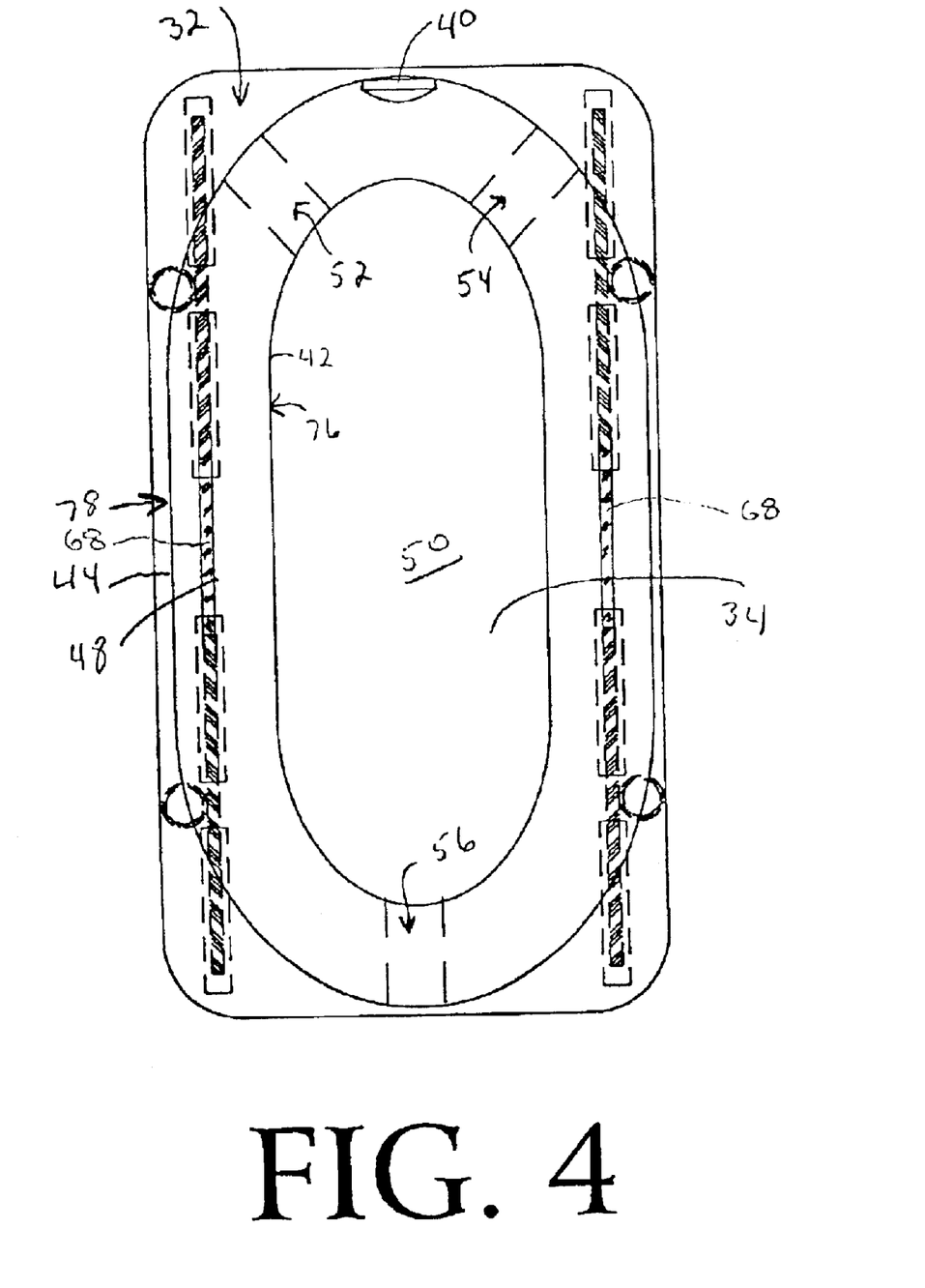
FIG. 4 is a bottom view of the preferred dam of the preferred wound shield shown in FIG. 2.

Referring now to the drawings wherein the showings are for the purpose of illustrating the preferred embodiments of the invention only, and not for purpose of limiting same, FIGS. 2–4 show a wound shield 30 including a hollow tubular inflatable dam 32, and a clear plastic window 34 attached to the dam 32. Dam 32 is formed of an inner peripheral surface or wall 42 which defines and surrounds a central opening 50. Dam 32 also includes an outer peripheral surface or a wall 44 connected to inner peripheral surface 42 by a rear or bottom body-engaging surface 48 and a front or top surface 46.

Dam 32 is provided with an irrigation aperture 52 extending from outer peripheral surface 44 through inner peripheral surface 42. Aperture 52 is adapted to receive or otherwise couple with an irrigation tube for providing communication between an irrigation system and central opening 50. Typically, the irrigation system provides an irrigation solution with medicinal characteristics for continuous or frequent cleansing of the wound. A drying aperture 54 is provided, which is adapted to receive or otherwise couple with a drying tube connected to an associated air supply. Drying aperture 54 provides communication between the air supply and central opening 50 for continuous or selective intermittent drying of the wound after irrigation. The drying aperture is also useful for connection to an associated source of vacuum (not shown) for use with VAC devices to apply a vacuum to the wound. A drainage aperture 56 is provided, preferably on a side of the dam opposite from the irrigation and drying apertures as shown. The drainage aperture is adapted to receive or otherwise couple with a drainage tube. The drainage tube could be connected to a pump, a collecting device, or a like device, to facilitate the removal of the irrigation solution, and dead skin and blood discharged from the wound. Both apertures 52 and 56 extend through the dam 32 from outer peripheral surface 44 through inner peripheral surface 42. These apertures can be plugged using suitable stoppers or the like when used as a VAC, when the patient is ambulatory, or as desired. It is to be appreciated that any of the apertures can be adapted for connection with an associated source of vacuum.

Dam 32 is preferably manufactured using a rotational casting or a rotational molding such as slush molding. The mold is typically made of aluminum but could be made of a variety of other metals. Dam 32 is formed from a soft liquid plastic, preferably vinyl, and the apertures are formed by extending a core pin through the mold, and removing the core pin after the liquid plastic cures.

Dam 32 further includes a soft self-sealing plug 40 preferably molded into the outer wall 44. Self-sealing plug 40 is adapted to receive a hypodermic needle used to inflate the dam 32 with air. The needle is inserted through the self-sealing plug 40 and the bulb is compressed to force air into the dam until the desired firmness of the dam 32 is obtained. The needle can be withdrawn at any time from the self-sealing plug 40 without any leakage of the air after removal. The self-sealing plug also allows for addition or removal of air at any time. Self-sealing plug 40 is preferably made of nitrile rubber.

Window 34 is made of a semi-hard clear plastic vinyl and has a generally flat planar bottom surface 33 and a generally flat top planar surface 35. In the embodiment illustrated, the window has an overall generally rectangular shape. Preferably, bottom planar surface 33 is attached to front surface 46 of the dam 32 using ultra-violet curable adhesive. However, various other types of adhesives could be used. Window 34 completely encloses central opening 50 of the dam 32 so that central opening 50 can remain airtight when the wound shield 30 is placed on the body of the patient, except for apertures 52, 54, and 56. It is preferred that window 34 encompass outer peripheral surface 44 of the dam 32 to increase the rigidity of the wound shield 30.

A pair of spaced apart connector assemblies 64 are disposed on top planar surface 35 of window 34 at opposite sides of the window. Connector assemblies 64 include a set of spaced apart co-axial tubes 66 holding a rod 68 that is connected to a set of eyelets 70. Tubes 66 are preferably made of plastic and could be bonded to top planar surface 35 of the window 34 or could be formed during the molding of window. Rods 68 and eyelets 70 are placed in tubes 66 prior to bonding or molding. Rod 68 and eyelet 70 are pivotable about an axis parallel to top planar surface 35, so that movement or twisting of the patient does not cause wound shield 30 to move from its position on the body of the patient. Further, connector assemblies are placed at a location outside central opening 50 to ensure that even pressure is applied to the entire perimeter of dam 32 when wound shield 30 is on the body of a patient. Rods 60 and eyelets 70 are preferably made of metal, but could be made of plastic or the like. The rods 68 extend completely across the face of the would shield 30 and in that way help prevent the shield from buckling in the middle during use such as along the line defined by section A—A in FIG. 2.

A pair of belts 36 and 38 are provided for holding wound shield 30 at a fixed location on the patient, so that central area 50 surrounds the wound. Belts 36 and 38 are preferably made of an elastic material, such as latex or neoprene foam, and are preferably non-absorbent and easy to clean. Each belt includes a first and a second connecting end 58. Each connecting end 58 includes a connecting portion 60 attached to the belt, and a hook portion 62 adapted to engage eyelet 70. It should be appreciated that in some circumstances, the wound shield may only need one belt because of the size or location of the wound. Further, the belt could be fixed at one end to a fixed connector on the wound shield, and be pivotable at the other end. It also should be appreciated that the releasable engagement of the belt and the connector assembly could employ connector types other than the preferred eye and hook arrangement.

With particular reference now to FIG. 3, dam 32 includes a ridge 72 extending angularly from inner peripheral surface 42 beyond and away from the bottom body-engaging surface 48. Dam 32 also includes a ridge 74 extending angularly from outer peripheral surface 44 beyond and away from the bottom body-engaging surface 48. Ridges 72 and 74 cooperate in holding wound shield 30 in a fixed position on the patient's body, even during movement and twisting of the patient. Further, ridges 72 and 74 seal central opening 50 and prevent any fluids or vacuum from escaping, and prevent contaminants from entering central area 50. Ridges 72 and 74 also alleviate the need to apply skin adhesives to the skin of the patient prior to applying the front body-engaging surface of the wound shield, while adding substantially to the cross-sectional rigidity of the dam 32.

With continued reference to FIG. 3, dam 32 preferably also includes a ridge 76 extending angularly from inner peripheral surface 42 beyond and away from top surface 46 and a ridge 78 extending angularly from outer peripheral surface 44 beyond and away from top surface 46. Ridges 76 and 78 aid in the adhesion process of front surface 46 to the back surface 33 of window 34. Additionally, ridges 76 and 78 increase the cross-sectional rigidity characteristic of dam 32, which helps prevent the center of the wound shield 30 from buckling after securing wound shield 30 on the body of a patient.

Figure 5:
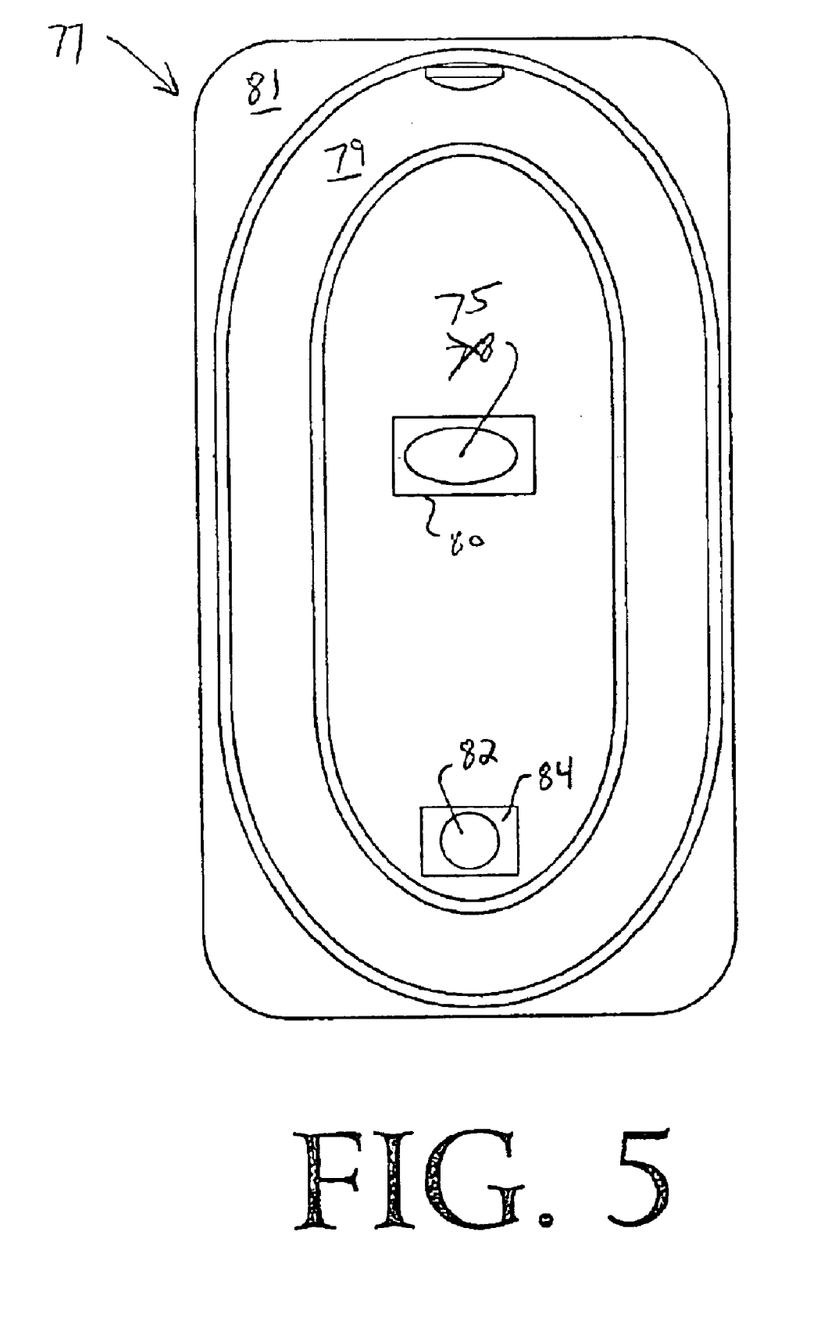
FIG. 5 is a bottom view of an alternative embodiment of the wound shield using cut outs in the window for irrigating, drying, and draining; and, FIG. 6 is a top view of an alternative embodiment of the invention.

It should be appreciated that in some cases, such as in stubborn wounds, more pressure is necessary for irrigation of the wound. It also should be appreciated that it is not always necessary to place irrigation aperture, drying aperture, and drainage aperture through the dam. For example, FIG. 5 shows a wound shield 77 having a dam 79 attached to a window 81. A first hole 75 is cut out of window 81 and covered over by a piece of adhesive tape 80 or plug. A second hole 82 is cut out of window 81 and covered by a piece of adhesive tape 84 or plug. The holes 75, 82 are adapted to receive the tip of an asepto syringe. Adhesive tape 80 or plug can be removed and irrigation solution can be communicated to the wound through hole 75 via large syringe, or the like. Further, an air source could be used to communicate air to the wound through hole 75 for drying the wound. Adhesive tape 84 or plug can be removed to provide drainage of irrigation solution, dead skin, and blood from central area 50. After cleansing, drying, and drainage, tape 80 and 84 or plug can be placed back over holes 75 and 82, respectively, protecting the wound from outside dirt or bacteria.

Figure 6:
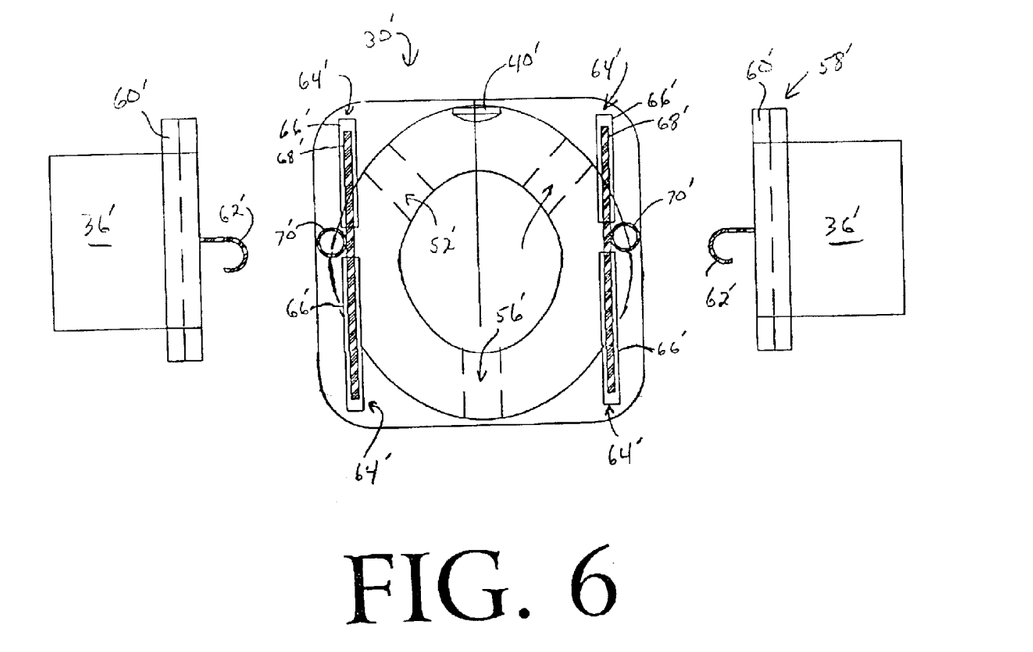

It should be noted that the shape of the wound shield could take on many forms, and the connector assemblies could be disposed on the window in a variety of different orientations. For example, FIG. 6 shows a wound shield 30' having an overall smaller size than the shield 30 shown in FIGS. 2–4. Only a single belt 36' is needed to receive the shield 30' to a patient. This type of wound shield could be useful for a wound near the groin area of an individual, such as one that would occur in a hernia operation or catheterization procedure. The wound shield 30' is formed and functions substantially identical to the shield 30 described above. Like parts are indicated in FIG. 6 with a primed (') suffix.

The foregoing descriptions are specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having thus described the invention, the following is claimed:

1. A wound shield for protecting and enclosing a wound that allows for selective irrigation of the wound with irrigation solution, selective drying of the wound, and to draw a vacuum as desired while also providing for selective drainage of the irrigation solution, said wound shield comprising:

a hollow inflatable tubular dam formed of an inner peripheral surface defining a central opening adapted to surround the wound of a patient, an outer peripheral surface defining the outermost extremity of said dam, a bottom body-engaging surface adapted to engage the patient and a front surface connecting said inner and outer peripheral surfaces together;

a semi-hard clear plastic window having a generally flat front planar surface and a generally flat rear planar surface, said flat rear planar surface being attached to said dam, such that said central opening is completely enclosed on the front surface of said dam by said window;

a first ridge extending from said dam in a direction away from the window and beyond the bottom body-engaging surface of said dam; and, a second ridge extending from said dam in a direction away from the window and beyond the bottom body-engaging surface of said dam.

2. The wound shield according to claim 1, further including an inner peripheral ridge disposed between said dam and said window and extending from the inner peripheral surface beyond the front surface of said dam towards said window, and an outer peripheral ridge disposed between said dam and said window and extending from the outer peripheral surface beyond the front surface of said dam towards said window.

3. The wound shield according to claim 1, further including:
- at least one irrigation aperture extending from said outer peripheral surface through said inner peripheral surface to said central opening, said irrigation aperture being adapted to receive a tube connected to an associated irrigation system;
- at least one drying aperture extending from said outer peripheral surface through said inner peripheral surface to said central opening, said drying aperture being adapted to receive a tube connected to an associated air source for drying the wound; and,
- at least one drainage aperture extending from said outer peripheral surface through said inner peripheral surface to said central opening, said drainage aperture being adapted to receive a tube connected to an associated drainage source.

4. The wound shield according to claim 1, further including at least one opening provided through said dam adapted for connection to an associated source of a vacuum to communicate said vacuum to said central opening.

5. The wound shield according to claim 1, wherein said window includes an irrigation and drying aperture located over said central opening for providing irrigation solution and drying of said wound and a drainage aperture located over said central opening below said irrigation and drying aperture for drainage of the irrigation solution.

6. A wound shield for protecting and enclosing a wound that allows for selective irrigation of the wound with irrigation solution, selective diving of the wound. and to draw a vacuum as desired while also providing for drainage of the irrigation solution, said wound shield comprising:
- a hollow inflatable tubular dam formed of an inner peripheral surface defining a central opening adapted to surround the wound of a patient, an outer peripheral surface defining the outermost extremity of said dam, a bottom surface adapted to engage the patient and a front surface connecting said inner and outer peripheral surfaces together;
- a semi-hard clear plastic window having a generally flat front planar surface and a generally flat rear planar surface, said flat rear planar surface being attached to said front surface of said dam, such that said central opening is completely enclosed on the front surface of said dam by said window;
- an inner peripheral ridge extending outwardly from the inner peripheral surface in a direction away from said window and beyond the bottom surface of said dam;
- an outer peripheral ridge extending outwardly from the outer peripheral surface in a direction away from said window and beyond the bottom surface of said dam; and,
- a plurality of connectors attached to said front planar surface of said clear plastic window, each connector being disposed at different locations outside said central opening and being adapted to be releasably attachable to a connecting end of a belt, wherein at least one connector is pivotable about an axis parallel to said front planar surface of said window.

7. The wound shield according to claim 6, further including:
- a belt having a first connecting end and a second connecting end and said plurality of connectors including at least a first connector releasably attachable to said first connecting end and a second connector being releasably attachable to said second connecting end.

8. The wound shield according to claim 1, wherein said window has an outside perimeter that is larger than the outer peripheral surface of said dam.

9. The wound shield according to claim 1, further including a self-sealing plug disposed on said dam and adapted to receive an associated hypodermic needle, wherein air can be forced into said dam through the hypodermic needle causing said dam to inflate, and said plug being adapted to seal itself upon removal of the associated hypodermic needle, so that the dam retains the air received by the hypodermic needle.

10. The wound shield for protecting and enclosing a wound that allows for selective vacuum, irrigation with irrigation solution and drying of the wound, while also providing for selective drainage of the irrigation solution, said wound shield comprising:
- a hollow inflatable tubular dam formed of an inner peripheral surface defining a central opening adapted to surround the wound, an outer peripheral surface defining the outermost extremity of said dam, and a bottom body-engaging surface and a front surface connecting said inner and outer peripheral surfaces to each other;
- a resilient clear window having a generally flat front planar surface and a generally flat rear planar surface, said flat rear planar surface being attached to said front surface of said dam such that said central opening is completely enclosed on the front surface of said dam by said window; and,
- a plurality of connectors attached to said front planar surface of said window, each connector being disposed at locations outside said central opening and being adapted to be releasably attachable to a connecting end of an associated belt, wherein at least one connector is pivotable about an axis parallel to said front planar surface of said window.

11. The wound shield according to claim 10, further including a belt having a first connecting end and a second connecting end, and said plurality of connectors including at least a first connector releasably attachable to said first connecting end and a second connector being releasably attachable to said second connecting end, wherein both of said first connector and said connector are pivotable about an axis parallel to said rear planar surface of said window.

12. The wound shield according to claim 11, wherein said first connecting end of said belt and said first connector include eye and hook connectors.

13. The wound shield according to claim 10, further including a self sealing plug disposed inside said dam and adapted to receive a hypodermic needle, wherein air can be forced into said dam through the hypodermic needle causing said dam to inflate, said plug being self-sealing to seal itself upon removal of the hypodermic needle therefrom so that the dam retains the air received by the hypodermic needle.

14. The wound shield according to claim 10, further including:
- at least one ridge extending outwardly from said dam in a direction away from the window and beyond the bottom body-engaging surface of said dam.

15. The wound shield according to claim 10, further including:

at least one irrigation aperture extending from said outer peripheral surface through said inner peripheral surface to said central opening, said irrigation aperture being adapted to receive a tube connected to an associated irrigation system;

at least one drying aperture extending from said outer peripheral surface through said inner peripheral surface to said central opening, said drying aperture being adapted to receive a tube connected to an associated air source for dying the wound; and, at least one drainage aperture extending from said outer peripheral surface through said inner peripheral surface to said central opening, said drainage aperture being adapted to receive a tube connected to an associated drainage source.

16. The wound shield according to claim 10, wherein said window includes an irrigation and drying aperture located over said central opening for providing irrigation solution and drying of said wound, and a drainage aperture located over said central opening below said irrigation and drying aperture for drainage of the irrigation solution.

17. The wound shield according to claim 10, wherein said window defines an outside perimeter that encompasses the outer peripheral surface of said dam.

18. A wound shield for protecting and enclosing a wound on an individual that allows for selected irrigation with irrigation solution and selected drying of the wound, while also providing for selected drainage of the irrigation solution, said wound shield comprising:

a tubular dam formed of an inner peripheral surface defining a central opening adapted to surround the wound of the individual, an outer peripheral surface defining the outermost extremity of said dam, and a rear body-engaging U-shaped surface defined by spaced apart ridges formed on the body-engaged surface and a front surface connecting said inner and outer peripheral surfaces to one another;

a clear plastic window having a generally flat front planar surface and a generally flat rear planar surface, said flat rear planar surface being attached to said front surface of said dam, such that said central opening is completely enclosed on the front surface of said dam by said window; and, a self-sealing plug disposed inside said dam and being adapted to receive an associated hypodermic needle, wherein air can be forced into said dam through the hypodermic needle causing said dam to inflate, and said plug being self-sealing to seal upon removal of the hypodermic needle so that the dam retains the air received by the hypodermic needle.

19. The wound shield according to claim 18, further including:

at least one irrigation aperture extending from said outer peripheral surface through said inner peripheral surface to said central opening, said irrigation aperture being adapted to receive a tube connected to an associated irrigation system;

at least one drying aperture extending from said outer peripheral surface through said inner peripheral surface to said central opening, said drying aperture being adapted to receive a tube connected to an associated air source for drying the wound; and, at least drainage aperture extending from said outer peripheral surface through said inner peripheral surface to said central opening, said drainage aperture being adapted to receive a tube connected to an associated drainage source.

20. The wound shield according to claim 18, wherein said window includes:

an irrigation and drying aperture located over said central opening for providing irrigation solution and drying of said wound; and, a drainage aperture located over said central opening below said irrigation and drying aperture.

21. A wound shield for protecting and enclosing a wound that allows for selective irrigation with irrigation solution and selective drying of the wound, while also providing for selective drainage of the irrigation solution, said wound shield comprising:

a tubular dam formed of an inner peripheral surface defining a central opening adapted to surround the wound, an outer peripheral surface defining the outermost extremity of said dam, a rear body-engaging surface, and a front surface;

a clear plastic window having a generally flat front planar surface and a generally flat rear planar surface, said flat rear planar surface being attached to said front surface of said dam, such that said central opening is completely enclosed on the front surface of said dam by said window; and, a self-sealing plug disposed inside said dam and being adapted to receive an associated hypodermic needle, wherein air can be forced into said dam through the hypodermic needle causing said dam to inflate, and said plug being self-sealing to seal upon removal of the hypodermic needle so that the dam retains the air received by the hypodermic needle; and, a plurality of connectors attached to said front planar surface of said clear plastic window, each connector being disposed at locations adjacent said central opening and being adapted to being releasably attachable to a connecting end of an associated belt, wherein at least one connector is pivotable about an axis parallel to said front planar surface of said window.

22. The wound shield according to claim 21, further including a belt having a first connecting end and a second connecting end, and wherein said plurality of connectors include at least a first connector releasably attachable to said first connecting end and a second connector being releasably attachable to said second connecting end.

23. In a wound shield comprising an annular dam having a central opening, said dam being fabricated wholly of soft, resilient and compressible non-absorbent material and having a top surface and a body-engaging bottom surface, a transparent and flexible window extending over and bridging the opening in said dam and sealingly secured to and carried by the top surface of said dam, the inner wall of said dam with the adjacent portion of said window forming an annular space, a first tube extending through said dam between the top and bottom surfaces of said dam and having one end in communication with said space and having the other end adapted for connection to an associated source of suction, and a second tube spaced from said first tube and extending through said dam between the top and bottom surfaces of said dam and having one end in communication with said space and having the other end adapted for connection to an associated source of medicament, the bottom surface of said dam sealingly engaging the skin of a human when the dam carrying the window and tubes is disposed so as to encompass an area surrounding a wound on said human to thereby house said wound within said space completely sealed from the outside air:

at least one ridge formed on the body-engaging bottom surface of said dam and extending outwardly in a direction substantially away from said window, the at least one ridge facilitating a vacuum in said annular space; and, a plurality of connectors attached to a front planar surface of said window, each connector being disposed at locations adjacent said central opening and being adapted to be releasably attachable to a connecting end of a belt, wherein at least one connector is pivotable about an axis parallel to said front planar surface of said window.

24. The wound shield according to claim 23, further including:

a plurality of ridges extending from said dam in a direction away from said window.

25. The wound shield according to claim 23, wherein said window defines an outside perimeter that encompasses the outer perimeter of said outer wall of said dam.

26. The wound shield according to claim 23, further including a self-sealing plug disposed inside said dam and being adapted to receive a hypodermic needle, wherein air can be forced into said dam through the hypodermic needle and said plug causing said dam to inflate, and said plug being self-healing to seal itself upon removal of the hypodermic needle therefrom, so that the dam retains the air received by the hypodermic needle.

27. The wound shield according to claim 23, further including a belt having a first connecting end and a second connecting end, and wherein said plurality of connectors include at least a first connector being releasably attachable to said first connecting end of said belt, and a second connector being releasably attachable to said second connecting end of said belt, wherein both of said first connector and said second connector are pivotable about an axis parallel to said front planar surface of said window.

28. An irrigation dressing for treatment of a wound on a patient, the irrigation dressing comprising:

a tubular dam defining a central opening adapted to surround the wound of said patient, a bottom surface adapted to engage the patient, and a front surface opposite said bottom surface;

a generally flat front planar member attached to said front surface of said dam; and, at least one ridge formed on the bottom surface of said dam.

29. The irrigation dressing according to claim 28, further including a second ridge formed on the bottom surface of said dam.

30. The irrigation dressing according to claim 28, further including:

at least one irrigation aperture provided on dam, said irrigation aperture being adapted to receive a tube connected to an associated irrigation system;

at least one drying aperture provided on said dam, said drying aperture being adapted to receive a tube connected to an associated air source delivering air to the wound; and, at least one drainage aperture provided on said dam, said drainage aperture being adapted to receive a tube connected to an associated drainage device.

31. The irrigation dressing according to claim 28, wherein said planar member includes irrigation and drying apertures for providing irrigation solution and air to said wound.

32. An irrigation dressing for treatment of a wound on a patient, the irrigation dressing comprising:

a tubular dam defining a central opening adapted to surround the wound of said patient, a bottom surface adapted to engage the patient, and a front surface opposite said bottom surface;

a generally flat front planar member attached to said front surface of said dam;

at least one ridge extending from the bottom surface of said dam; and, a plurality of connectors attached to said front planar member, each connector being adapted for releasable attachment to a connecting end of an associated belt, wherein at least one connector is pivotable about an axis parallel to said front planar member.

* * * * *